(12) United States Patent
Jackson

(10) Patent No.: US 7,122,628 B2
(45) Date of Patent: Oct. 17, 2006

(54) PROCESS FOR THE SYNTHESIS OF A PEPTIDE HAVING A TRP RESIDUE

(75) Inventor: Steven Allen Jackson, Newtonville, MA (US)

(73) Assignee: Ipsen Manufacturing Ireland, Limited, Dublin (IE)

( * ) Notice: Subject to any disclaimer, the term of this patent is extended or adjusted under 35 U.S.C. 154(b) by 206 days.

(21) Appl. No.: 10/451,486

(22) PCT Filed: Dec. 19, 2001

(86) PCT No.: PCT/IE01/00159

§ 371 (c)(1),
(2), (4) Date: Nov. 24, 2003

(87) PCT Pub. No.: WO02/051861

PCT Pub. Date: Jul. 4, 2002

(65) Prior Publication Data

US 2004/0077827 A1    Apr. 22, 2004

(30) Foreign Application Priority Data

Dec. 22, 2000 (IE) ................................ 2000/1079

(51) Int. Cl.
*C07K 1/00* (2006.01)
*C07K 1/06* (2006.01)
*C07K 1/14* (2006.01)
*C07K 1/107* (2006.01)
*C07K 7/04* (2006.01)

(52) U.S. Cl. .............. 530/333; 530/334; 530/335; 530/337; 530/344; 530/345; 530/328

(58) Field of Classification Search .............. 530/313, 530/333–337, 345
See application file for complete search history.

(56) References Cited

U.S. PATENT DOCUMENTS 4,211,693 A    7/1980   Rivier et al.
4,569,927 A    2/1986   Rivier et al.

FOREIGN PATENT DOCUMENTS

| BE | 904.458     | 3/1986  |
|----|-------------|---------|
| DE | 39 31 731 A | 3/1990  |
| EP | 0 162 575   | 11/1985 |
| JP | 05-331188   | 12/1993 |

OTHER PUBLICATIONS

G. Flouret, et al. J. Med. Chem. (1992) 35, pp. 636-640.*
M. Manning. J. Am. Chem. Soc. (1968) 90(5), pp. 1348-1349.*
Mery, J. et al., "Tryptophan Reduction and Histidine Racemization During Deprotection by Catalytic Transfer Hydrogenation and of an Analog of the Luteinizing Hormone Releasing Factor," Int. J. of Peptide and Protein Res. 1988, 31 (4):412-419, XP008005285.
Pineda, J. L. et al., "Effect of GnRH Antagonist [ac-delta-3Pro-1, pFDPhe-2, DTrp-3, 6] GnRH, on Pulsatile Gonadotrop in Secretion in the Castrate Male Primate," J. Clin. Endocrinology and Metabolism, 1983, 56(2):420-422, XP008005269.
Coy, D. H. et al., "Minimal side-chain protection can be a successful strategy in solid-phase peptide synthesis," Int. J. Peptide Protein Res., 1979, 14:339-343.
Pipkorn, R. et al., "Histidine racemization in the synthesis of an analog of the lutenizing hormone releasing factor," Int. J. Pep. Protein Res., 1986, 27:583-588.

* cited by examiner

*Primary Examiner*—Cecilia J. Tsang
*Assistant Examiner*—Andrew D. Kosar
(74) *Attorney, Agent, or Firm*—Yankwich & Associates; Alan F. Feeney; Pamela C. Ball

(57) ABSTRACT

A process for the solid phase synthesis of a peptide having at least one thyptophan residue, wherein said method comprises temporarily protecting the indole ring of said tryptophan residue with a side chain protecting group which is labile to a base wherein said protecting group is removed during cleavage of said peptide from the solid support.

12 Claims, No Drawings

PROCESS FOR THE SYNTHESIS OF A PEPTIDE HAVING A TRP RESIDUE

TECHNICAL FIELD

This invention relates to a process for the synthesis of a peptide having a Trp residue using a solid phase.

BACKGROUND ART

Luteinizing hormone-releasing hormone (LHRH) is a neurotransmitter produced by the hypothalamus which stabilizes the secretion of luteinizing hormone (LHRH) and follicle-stimulating hormone (FSH) from the pituitary, which in turn stimulates the synthesis of steroid hormones, such as testosterone, from the gonads. Many LHRH peptide analogs (e.g., agonists and antagonists) are currently sold for the treatment of endometriosis, prostate cancer, precocious puberty, and other hormonally mediated disorders. The synthesis of such LHRH analogs are difficult and expensive.

Solid phase peptide synthesis was introduced in 1963 with the intent to overcome many of the intermediate purification problems associated with solution phase peptide synthesis. Stewart, et al., Solid Phase Peptide Synthesis (Pierce Chemical Co., 2d ed.) 1984. During solid phase synthesis, amino acids are assembled (i.e., coupled) into a peptide of any desired sequence while one end of the chain (i.e., the C-terminus) is anchored to an insoluble support. Once the desired sequence has been linked together on the support, the peptide is then detached (i.e., cleaved) from the support.

U.S. Pat. No. 4,010,125 (1977) describes the synthesis of [D-Trp$^6$]-LHRH in which the side chains of four of the ten residues of the LHRH agonist are protected (e.g., L-histidyl (tosyl), seryl(benzyl), tyrosyl(2,6-di-Cl-Bzl), and L-arginyl (tosyl)). However, Coy, et al., Int. J. Peptide Protein Res. 14:359 (1979) later reported the synthesis of a number of other LHRH analogs in which minimal side chain protection, e.g., only salt protection of arginine (i.e., Arg.HCl), produced superior yield to the corresponding protected synthesis. The present invention is directed to the discovery that, despite the trend in the art to not protect the side chains of amino acids in the synthesis of LHRH analogs, the protection of the tryptophan residue during solid phase synthesis does indeed improve the yield of LHRH analogs having a tryptophan residue (e.g., [D)-Trp$^6$]LHRH).

DISCLOSURE OF INVENTION

In one aspect, the present invention provides a process for making a peptide of the formula (I),

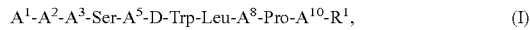

A$^1$-A$^2$-A$^3$-Ser-A$^5$-D-Trp-Leu-A$^8$-Pro-A$^{10}$-R$^1$,   (I)

wherein
A$^1$ is pGlu or N-Ac-D-β-Nal;
A$^2$ is His, D-p-Cl-Phe, or D-p-F-Phe;
A$^3$ is Trp or D-Trp;
A$^5$ is Tyr, NicLys, cPzACAla, or PicLys;
A$^8$ is Arg, hArg(Et)$_2$, hArg(Bu), hArg(CH$_2$CF$_3$)$_2$, or Lys (iPr);
A$^{10}$ is Gly, D-Ala or is deleted; and
R$^1$ is NH$_2$ or NHEt;
which comprises the steps of:
(a) attaching a cesium-salt of Boc-A$^{10}$, if A$^{10}$ is present, or Boc-Pro if A$^{10}$ is not present, onto a chloromethylated polystyrene resin to yield Boc-A$^{10}$-resin or Boc-Pro-resin, respectively;

(b) deblocking Boc-A$^{10}$-resin or Boc-Pro-resin by mixing the Boc-A$^{10}$-resin or Boc-Pro-resin with a mixture of a Boc-deblocking organic acid to yield an organic acid salt of H$_2$N-A$^{10}$-resin or an organic acid salt of H$_2$N-Pro-resin, respectively;

(c) neutralizing the organic acid salt of H$_2$N-A$^{10}$-resin or the organic acid salt of H$_2$N-Pro-resin with a base to yield H$_2$N-A$^{10}$-resin or H$_2$N-Pro-resin, respectively;

(d) coupling H$_2$N-A$^{10}$-resin or H$_2$N-Pro-resin with a Boc-α-amine protected amino acid, said protected amino acid corresponding to the amino acid defined for formula (I) in the order shown from the C-terminal to the N-terminal, which comprises,
  (i) reacting H$_2$N-A$^{10}$-resin or H$_2$N-Pro-resin with the Boc-α-amine protected amino acid in the presence of a peptide coupling agent to yield a Boc-blocked coupled product;
  (ii) deblocking the Boc group from the Boc-blocked coupled product by mixing the Boc-blocked coupled product with a Boc-deblocking organic acid to yield a coupled product;
  (iii) reacting the coupled product with a next Boc-α-amine protected amino acid in the presence of a peptide coupling agent to yield a Boc-blocked coupled product;
  (iv) deblocking the Boc group from the Boc-blocked coupled product by mixing the Boc-blocked coupled product with a Boc-deblocking organic acid to yield a next coupled product;
  (v) repeating steps (d)(iii) and (d)(iv) until the N-terminal amino acid of the peptide of formula (I) has been coupled and the Boc group of the N-terminal amino acid has been deblocked to yield a protected completed peptide-resin;

(e) cleaving and deprotecting the protected completed peptide-resin to yield the peptide of formula (I), which comprises:
  (i) making a solution of the protected completed peptide-resin in an alcohol/inert polar aprotic solvent mixture;
  (ii) cooling the solution to about 0° C. to about 10° C.;
  (iii) bubbling ammonia gas or ethylamine gas slowly into the solution and maintaining cooling until the solution is well saturated with ammonia to yield a saturated solution;
  (iv) mixing the saturated solution without cooling for about 15–36 hours until >95% of free methyl ester is converted to the corresponding amide, when ammonia gas is used, or the corresponding ethylamide, when ethylamine gas is used; and
  (f) isolating said peptide from said solution.

A preferred process of the foregoing process is where A$^{10}$ is Gly.

A preferred process of the immediately foregoing process is where the following Boc-α-amine amino acids are coupled successively from the C-terminal to the N-terminal, N-α-Boc-L-proline, N-α-Boc-L-arginine.HCl, N-α-Boc-L-leucine, N-α-Boc-D-tryptophan(N'-indole-formyl), N-α-Boc-L-tyrosine, N-α-Boc-L-serine hydrate, N-α-Boc-tryptophan(N'-indole-formyl), N-α-Boc-L-histidine(tosyl)-cyclohexylamine salt, and pyroglutamic acid.

A preferred process of the immediately foregoing process is where the formyl protecting group of the Trp side chain is removed by treatment with a solution comprising ammonia, a primary amine, or a secondary amine and an alcohol.

A preferred process of the immediately foregoing process is where said solution comprises ammonia and methanol.

A preferred process of the immediately foregoing process is where the step of isolating said peptide from said solution comprises:
(i) filtering said solution to produce a filtrate; and
(ii) concentrating said filtrate.

A preferred process of the immediately foregoing process is where said peptide of formula (I) is pGlu-His-Trp-Ser-Tyr-D-Trp-Leu-Arg-Pro-Gly-NH$_2$.

A preferred process of the immediately foregoing process is where 1-hydroxybenzotriazole (HOBT) is also used when coupling N-α-Boc-D-tryptophan(N'-indole-formyl), N-α-Boc-L-tyrosine, N-α-Boc-L-serine hydrate and N-α-Boc-tryptophan(N'-indole-formyl).

In another aspect, the present invention provides a process for the solid phase synthesis of a peptide of formula (II),

$$A^1\text{-}A^2\text{-}A^3\text{-}Ser\text{-}A^5\text{-}A^6\text{-}Leu\text{-}A^8\text{-}Pro\text{-}A^{10}\text{-}R^1, \quad (II)$$

wherein
$A^1$ is pGlu or N-Ac-D-β-Nal;
$A^2$ is His, D-p-Cl-Phe, or D-p-F-Phe;
$A^3$ is Trp, D-Trp, D-β-Nal, or D-Pal;
$A^5$ is Tyr, NicLys, cPzACAla, or PicLys;
$A^6$ is D-β-Nal, D-hArg(Et)$_2$, D-Lys(iPr), D-hArg(Bu), D-hArg(CH$_2$CF$_3$)$_2$, D-His(Bzl), D-Leu, D-Pal, D-Ser (tBu), D-Trp, D-Cit, D-Arg, D-NicLys, D-PicLys, or D-Qal;
$A^8$ is Arg, hArg(Et)$_2$, hArg(Bu), hArg(CH$_2$CF$_3$)$_2$, or Lys (iPr);
$A^{10}$ is Gly, NHNHCO or D-Ala or is deleted; and
$R^1$ is NH$_2$ or NHEt;

wherein at least one of $A^3$ or $A^6$ is Trp or D-Trp, and said method comprises temporarily protecting any tryptophan residue with a side chain protecting group which is labile to a base wherein said protecting group is removed during cleavage of the peptide of formula (II) from the solid support by reaction with a base.

A preferred process of the immediately foregoing process is where said Trp or D-Trp side chain protecting group is an acyl group.

A preferred process of the immediately foregoing process is where said Trp or D-Trp side chain protecting group is removed by treatment with a solution comprising ammonia, a primary amine, or a secondary amine and an alcohol.

Another preferred process of the immediately foregoing process is where said side chain protecting group is formyl and said base is a methanol solution comprising ammonia.

A preferred process of the immediately foregoing process is where $A^3$ is Trp.

A preferred process of the immediately foregoing process is where $A^1$ is pGlu, $A^2$ is His, $A^5$ is Tyr, $A^6$ is D-Trp, $A^8$ is Arg, $A^{10}$ is Gly, and $R^1$ is NH$_2$.

In yet another aspect, the present invention is directed to a process for the solid phase synthesis of the peptide of the formula pGlu-His-Trp-Ser-Tyr-D-Trp-Leu-Arg-Pro-Gly-NH$_2$ comprising the steps of successively coupling onto a solid support the following protected amino acids: Boc-Gly, Boc-Pro, Boc-Arg.HCl, Boc-Leu, Boc-D-Trp(PG-1), Boc-Tyr, Boc-Ser, Boc-Trp(PG-1), Boc-His(PG-2), and Boc-pGlu, where PG-1 is a protecting group labile to a base and PG-2 is a protecting group for His, and said process comprises both cleaving said peptide from said support and removing said PG-1 from said tryptophan residues with a solution comprising a base.

A preferred process of the immediately foregoing process is where said PG-1 is an acyl group.

A preferred process of the immediately foregoing process is where said solution comprises ammonia, a primary amine, or a secondary amine.

A preferred process of the immediately foregoing process is where said PG-2 is tosyl.

A preferred process of the immediately foregoing process is where said PG-1 is formyl and said solution comprises ammonia.

Other features and advantages of the present invention will be apparent from the detailed description of the invention, and from the claims.

ABBREVIATIONS

BOC=t-butoxycarbonyl
Cit=citrulline
cPzACAla=cis-3-(4-pyrazinylcarbonylaminocyclohexyl) alanine
hArg(Bu)=N-guanidino-(butyl)-homoarginine
hArg(Et)$_2$=N,N'-guanidino-(dimethyl)-homoarginine
hArg(CH$_2$CF$_3$)$_2$=N,N'-guanidino-bis-(2,2,2-trifluoroethyl)-homoarginine
HOBT=1-Hydroxybenzotriazole
Lys(iPr)=N$^\epsilon$-isopropyllysine
β-Nal=β-1-naphthylalanine or β-2-naphthylalanine, unless otherwise indicated
NicLys=N$^\epsilon$-nicotinoyllysine
Pal=pyridylalanine
p-Cl-Phe=3-(4-chlorophenyl)alanine
p-F-Phe=3-(4-fluorophenyl)alanine
PicLys=N$^\epsilon$-picolinoyllysine
Qal=quinolylalanine It is believed that one skilled in the art can, based on the description herein, utilize the present invention to its fullest extent. The following specific embodiments are, therefore, to be construed as merely illustrative, and not as a limitation of the scope of the invention.

Unless defined otherwise, all technical and scientific terms used herein have the same meaning as commonly understood by one of ordinary skill in the art. All publications, patent applications, patents, and other references mentioned herein are expressly incorporated by reference.

A peptide of the formula (I) can be prepared by solid phase peptide synthesis using Boc chemistry on Merrifield resin followed by cleavage of the peptide from the resin with ammonia, a primary amine or a secondary amine in an alcohol to yield the title peptide.

The first step in such a process according to the invention is to attach the cesium-salt of the C-terminal amino acid, Boc-A$^{10}$, onto Merrifield resin through an ester linkage. The cesium salt of Boc-A$^{10}$ is formed by adding Boc-A$^{10}$ to cesium carbonate in a mixture of methanol and water. The cesium salt of the Boc-A$^{10}$ is dried under vacuum and then allowed to react with the chloromethyl benzyl groups on the polystyrene in an anhydrous polar aprotic solvent such as dimethylformamide (DMF). This reaction is run for about 24 to 48 hours, preferably 36 hours at about 45° C. to 60° C., preferably 50° C. The reacted resin is then filtered, rinsed with water, a polar aprotic solvent such as DMF, and an alcohol such as methanol, and then dried to a constant weight preferably under reduced pressure. The dried resin can be tested to determine the Boc-A$^{10}$ content which is expressed in mmoles of A$^{10}$ per dry gram of resin. The calculated value is used to determine the scale of the assembly reaction for subsequent material usage and theoretical yield calculations.

Synthesis of a peptide of formula (I) can be performed on the Boc-$A^{10}$-resin contained in a glass reactor with sintered glass disk filters at the bottom of the reactor. The reactor is stirred with a mechanical stirrer and drained by applying inert gas pressure such as nitrogen pressure to force liquids through the sintered disc at the bottom while retaining the resin in the reactor. First, the Boc group of Boc-$A^{10}$ is removed (e.g., deblocked) from the $A^{10}$-resin by mixing the $A^{10}$-resin twice with a mixture of an organic acid in a chlorinated solvent, preferably 25% trifluoroacetic acid (TFA) in dichloromethane (DCM), first for about 2 minutes and then for about 25 minutes followed by draining aided by nitrogen pressure. The $A^{10}$-resin is rinsed three times with DCM and two times with an alcohol, such as isopropyl alcohol (IPA), and the resulting amino-TFA salt is neutralized twice with a base in an inert solvent, preferably 10% triethylamine base in DCM, for about 5 minutes each and rinsed again three times with DCM. The resin is, then coupled with 2.5 molar equivalent mixtures of Boc α-amino protected amino acids, corresponding to the amino acids defined for formula (I) going from the C-terminal end to the N-terminal end, using a peptide coupling agent, preferably diisopropylcarbodiimide (DIC), in polar aprotic solvents, preferably DMF/DCM mixtures as a reaction media. Each coupling is followed by rinses with DMF and DCM. The resin can be tested by Kaiser Ninhydrin for each coupling completion except for Arginine which can be tested using isatin to detect the secondary amine of residual uncoupled Proline. The Boc group is removed from each coupled amino acid following testing as described above. The following protected amino acids corresponding to the amino acids of formula (I) are preferably used in a synthesis of the present invention: N-α-Boc-L-Proline, N-α-Boc-L-Arginine-HCl, N-α-Boc-L-Leucine, N-α-Boc-D-Tryptophan(N'-indole-formyl), N-α-Boc-L-Tyrosine, N-α-Boc-L-Serine hydrate, N-α-Boc-L-Histidine(tosyl)-cyclohexylamine salt, and Pyroglutamic acid.

1-Hydroxybenzotriazole (HOBT) can also be used (3–5 eq.) when coupling the protected derivatives of D-Trp, Tyr, Ser, and Trp. The tosyl side chain protecting group of Histidine is removed with two treatments of HOBT in DMF for one hour (each) after the final amino acid coupling. Boc-D-Tryptophan and Boc-L-Tryptophan are side chain protected with formyl on the nitrogen of the indole ring. The formyl is later removed during cleavage of the peptide from the resin using a base.

The completed peptide-resin is rinsed into a tared sintered glass funnel with an inert chlorinated solvent such as DCM, rinsed twice with an alcohol such as methanol, and dried under vacuum. The dried peptide-resin is transferred to a one liter, three-neck, round bottom flask. A mixture of 9:1 methanol/DMF at about 15 milliliters per gram of the peptide-resin is added to the round bottom flask. The solution is cooled to about <10° C., and, if the C-terminal amide form of the peptide is desired, ammonia gas is slowly bubbled with strong cooling until well saturated (about 1 hour addition time), wherein the peptide is liberated from the resin in the form of a free methyl ester intermediate. The solution is allowed to further mix without cooling for about 15–36 hours during which time approximately >95% of the free methyl ester is converted to the corresponding amide product. Reaction progress may be monitored, e.g., by using high pressure liquid chromatography (HPLC), and may be terminated when the desired extent of completion is attained. The product is filtered in solution with a sintered glass funnel, and the resin is rinsed with methanol and DMF several times. All rinses and filtrates are condensed to a very thick oil. Ethyl acetate is added and the solution is triturated to solidify the product, decanted, and trituration is repeated again with ethyl acetate. The crude product is dissolved into methanol and an equal volume of 4N acetic acid is added. The solution is concentrated to remove all methanol. The product is diluted with 4N acetic acid.

The C-terminal ethylamide form of the peptide can be obtained by substituting ethylamine for ammonia in the procedure of the immediately foregoing paragraph, wherein the temperature the solution is maintained below about <16° C. during saturation of the solution with ethylamine, and preferably between about 5° C. to about 15° C.

The crude material can be purified by repeated reverse phase preparative chromatographic runs and lyophilized to give the final product.

It will be apparent to one skilled in the art that other solvent systems may be used, including, but not limited to, low molecular weight alcohols such as ethanol, propanol, isopropanol, butanol, isobutanol, tert-butanol, and the like, other polar aprotic solvents, and mixtures thereof.

MODES FOR CARRYING OUT THE INVENTION

The following example is described for purposes of illustrating a method of the present invention and is not to be construed to limit the present invention in any way.

EXAMPLE

Synthesis of pGlu-His-Trp-Ser-Tyr-D-Trp-Leu-Arg-Pro-Gly-$NH_2$ ([D-$Trp^6$]LHRH-$NH_2$)

[D-$Trp^6$]LHRH-$NH_2$ was prepared by solid phase peptide synthesis using Boc chemistry on Merrifield resin followed by cleavage of the peptide from the resin with methanolic ammonia to yield the title peptide.

The first step in the process was to attach the cesium-salt of the C-terminal amino acid, Boc-glycine, to the Merrifield resin through an ester linkage. The cesium salt of Boc-glycine is formed by reacting Boc-glycine (40.9 g) with cesium carbonate (37.9 g) in a mixture of methanol and water (80 ml/40 ml). The cesium salt of the Boc-glycine was dried under vacuum and then allowed to react with the chloromethyl benzyl groups on the polystyrene beads (Merrifield resin; Advanced Chemtech, 88.2 g) in anhydrous dimethylformamide (DMF; 200 ml). This reaction was run for about 36 hours at about 50° C. on a Buchi™ Model 110 rotary evaporator. The reacted resin was then filtered, rinsed with water, DMF, and methanol, and was then dried to a constant weight at T<35° C. in vacuo. The dried resin was then tested to determine the Boc-glycine content which is expressed in mmoles of glycine per dry gram of resin. The calculated value of 0.872 mmoles/gram was found and used to determine the exact scale of the assembly reaction for subsequent material usage and theoretical yield calculations.

Synthesis of the peptide was performed on the Boc-glycine resin (12.5 g) contained in a 500 ml glass reactor with sintered glass disk filters at both the bottom and top of the reactor. The reactor was filled from the bottom and shaken by inversion (rotating 180 degrees in 3 seconds). First, the Boc group was removed (e.g., deblocked) from the glycine resin by mixing the resin twice with 175 ml of 25% trifluoroacetic acid (TFA) in dichloromethane (DCM) (2 minutes and 25 minutes) followed by draining aided by nitrogen pressure. The resin was rinsed three times with 125 ml of DCM and two times with 125 ml of isopropyl alcohol (IPA) and then three times with 125 ml of DCM. The resulting amino-TFA salt was neutralized twice with 125 ml of 10% triethylamine base in DCM for five minutes each and rinsed again three times with DCM.

The resin was then coupled and deblocked with 2.5 molar equivalent mixture of the following Boc protected amino acid with 4.2 ml of diisopropylcarbodiimide (DIC) in 16 ml of DMF and 47 ml of DCM; 5.84 g Boc-L-Proline, 8.93 g Boc-L-Arginine.HCl, 6.77 g Boc-L-Leucine, 9.0 g Boc-D-Tryptophan(formyl), 7.64 g Boc-L-Tyrosine, 9.0 g Boc-L-Tryptophan(formyl), 6.06 g Boc-L-Serine hydrate, 16 g Boc-L-Histidine(tosyl).cyclohexylamine salt, and 13.5 g pyroglutamic acid. 1-Hydroxybenzotriazole (HOBT) was also used (3–5 eq.) in D-Trp, Tyr, Ser, and Trp couplings. 75 ml of dimethylacetamide (DMA) was used in place of DMF and DCM in coupling Arg. The resin was rinsed with DMF and DCM and tested by Kaiser-Ninhydrin for coupling completion. The Boc group was removed from each coupled amino acid as described above. Histidine was side chain protected with tosyl which was removed with two treatments of 4.16 g of HOBT in 105 ml of DMF for one hour (each) after the final amino acid coupling. Boc-D-Tryptophan and Boc-L-Tryptophan were side chain protected with formyl which was removed during cleavage of the peptide from the resin.

The completed peptide-resin was rinsed into a tared sintered glass funnel with DCM, rinsed twice with methanol, and dried under vacuum. The dried peptide-resin was transferred to a one liter, three-neck, round bottom flask. 15 ml/gram of the peptide resin in 9:1 methanol/DMF (380 ml for 10.9 mM scale) was added to the flask. The solution was cooled to about <10° C., and ammonia gas was slowly bubbled with strong cooling until well saturated (about 1 hour addition time). The solution was allowed to further mix without cooling for about 15–36 hours until >95% of free methyl ester was converted to amide product as determined by monitoring with high pressure liquid chromatography (HPLC). The product was filtered in solution with a sintered glass funnel, and the resin was rinsed with methanol and DMF several times. All rinses and filtrates were condensed to a very thick oil on a rotary evaporator at T<40° C. Ethyl acetate (0.08 liters) was added and the solution was triturated to solidify the product, decanted, and repeated with 0.08 liters of ethyl acetate. The hard, gummy product was soaked in ethyl acetate overnight and decanted. The crude product was dissolved into methanol (0.07 liters) and an equal volume of 4N acetic acid was added. The solution was concentrated to remove all methanol on a rotary evaporator at T<40° C. The product was diluted to approximately 35 grams product/liter with 4N acetic acid.

The crude material was then purified by repeated reverse phase chromatographic runs and lyophilized to give the final product (8.4 gm, 59% yield) as a white solid at >99% purity.

OTHER EMBODIMENTS

From the above description, one skilled in the art can easily ascertain the essential characteristics of the present invention, and without departing from the spirit and scope thereof, can make various changes and modifications of the invention to adapt it to various uses and conditions. Thus, other embodiments are also within the claims.

The invention claimed is:

1. A process for making a peptide of the formula (I), $$\rho Glu\text{-}His\text{-}Trp\text{-}Ser\text{-}Tyr\text{-}D\text{-}Trp\text{-}Leu\text{-}Arg\text{-}Pro\text{-}Gly\text{-}NH_2, \quad (I)$$

wherein said process comprises:
(a) temporarily protecting the indole-NH group on the side chain of any tryptophan residue with a side chain protecting group;
(b) temporarily protecting the side chain of the histidine residue with a side chain protecting group;
(c) attaching a cesium salt of Boc-Gly onto a chloromethylated polystyrene resin to yield Boc-Gly resin;
(d) deblocking Boc-Gly-resin by mixing the Boc-Gly-resin with a mixture of a Boc-deblocking organic acid to yield an organic acid salt of $H_2N$-Gly-resin;
(e) neutralizing the organic acid salt of $H_2N$-Gly-resin with a base to yield $H_2N$-Gly-resin;
(f) successively coupling $H_2N$-Gly-resin with a Boc-α-amine protected amino acid, said protecting amino acid corresponding to ρGlu-His-Trp-Ser-Tyr-D-Trp-Leu-Arg-Pro-Gly-$NH_2$ in the order shown from the C-terminal to the N-terminal, wherein said coupling comprises:
  (i) reacting $H_2N$-Gly-resin with the Boc-α-amine protected amino acid in the presence of a peptide coupling agent to yield a Boc-blocked coupled product;
  (ii) deblocking the Boc group from the Boc-blocked coupled product by mixing the Boc-blocked coupled product with a Boc-deblocking organic acid to yield a coupled product;
  (iii) reacting the coupled product with a next Boc-α-amine protected amino acid in the presence of a peptide coupling agent to yield a Boc-blocked coupled product;
  (iv) deblocking the Boc group from the Boc-blocked coupled product by mixing the Boc-blocked coupled product with a Boc-deblocking organic acid to yield a next coupled product;
  (v) repeating steps (d)(iii) and (d)(iv) until the N-terminal amino acid of the peptide of formula (I) has been coupled and the Boc group of the N-terminal amino acid has been deblocked to yield a protected completed peptide-resin;
  (vi) removing said side chain protecting group on the histidine residue;
(g) deprotecting the protected indole-NH group on the side chains of the tryptophan residues and cleaving the completed peptide-resin to yield ρGlu-His-Trp-Ser-Tyr-D-Trp-Leu-Arg-Pro-Gly-$NH_2$, wherein said deprotecting and cleaving comprises:
  (i) making a solution of the protected completed peptide-resin in an alcohol/inert polar aprotic solvent mixture;
  (ii) cooling the solution to about 0° C. to about 10° C.;
  (iii) bubbling ammonia gas slowly and maintaining cooling until the solution is well saturated with ammonia to yield a saturated solution;
  (iv) mixing the saturated solution without cooling for about 15–36 hours until <95% of free methyl ester is converted to the corresponding amide; and
(h) isolating ρGlu-His-Trp-Ser-Tyr-D-Trp-Leu-Arg-Pro-Gly-$NH_2$ from said solution.

2. A process of claim 1 wherein the indole-NH groups on the side chains of the tryptophan residues are temporarily protected with a formyl group and the side chain of the histidine residue is temporarily protected with a tosyl group.

3. A process according to claim 2, wherein the following Boc-α-amine amino acids are coupled successively from the C-terminal to the N-terminal, N-α-Boc-L-proline, N-α-Boc-L-arginineHCl, N-α-Boc-L-leucine, N-α-Boc-D-tryptophan (N'-indole-formyl), N-α-Boc-L-tyrosine, N-α-Boc-L-serine hydrate, N-α-Boc-tryptophan(N'-indole-formyl) and N-α-Boc-L-histidine(tosyl)-cyclohexylamine salt to yield a coupled product and further wherein pyroglutamic acid is coupled to the N-terminal of said coupled product.

4. A process according to claim 3 wherein said pyroglutamic acid is temporarily protected with a Boc protecting group.

5. A process according to claim 1, wherein said indole-NH group of the side chains of any tryptophan residue is protected with an acyl group.

6. A process according to claim 5, wherein said side chain protecting group is a formyl group.

7. A process according to claim 6, wherein the formyl protecting groups of the side chains of the tryptophan residues are removed by treatment with a solution comprising a) ammonia, a primary amine, or a secondary amine and b) an alcohol.

8. A process according to claim 7, wherein said solution comprises ammonia and methanol.

9. A process according to claim 8, wherein 1-hydroxybenzotriazole (HOBT) is used when coupling N-α-Boc-D-tryptophan(N'-indole-formyl), N-α-Boc-L-tyrosine, N-α-Boc-L-serine hydrate and N-α-Boc-tryptophan (N'-indole-formyl).

10. A process according to claim 5, wherein said acyl group is removed by treatment with a solution comprising a) ammonia, a primary amine, or a secondary amine and b) an alcohol.

11. A process of claim 1, wherein said side chain protecting group on the histidine residue is a tosyl group.

12. A process according to claim 11, wherein the tosyl protecting group of the side chain of the histidine residue is removed by treatment with a solution comprising 1-Hydroxybenzotriazole (HOBT) in dimethylformamide (DMF).

* * * * *

UNITED STATES PATENT AND TRADEMARK OFFICE
CERTIFICATE OF CORRECTION

| | | |
|---|---|---|
| PATENT NO. | : 7,122,628 B2 | Page 1 of 1 |
| APPLICATION NO. | : 10/451486 | |
| DATED | : October 17, 2006 | |
| INVENTOR(S) | : Steven Allen Jackson | |

It is certified that error appears in the above-identified patent and that said Letters Patent is hereby corrected as shown below:

In the claims

Claim 1, column 8, line 56, that portion of the claim which reads "about 15-36 hours until <95% of free methyl ester is" should read -- about 15-36 hours until >95% of free methyl ester is --

Claim 3, column 8, line 67, that portion of the claim which reads "L-arginineHCl," should read -- L-arginine•HCl, --

Signed and Sealed this

Twenty-third Day of January, 2007

JON W. DUDAS
*Director of the United States Patent and Trademark Office*